(12) United States Patent
Alavi et al.

(10) Patent No.: US 11,905,392 B2
(45) Date of Patent: Feb. 20, 2024

(54) UREA-GLYOXAL CROSSLINKING COMPOUNDS FOR PHENOLIC BINDER COMPOSITIONS

(71) Applicant: JOHNS MANVILLE, Denver, CO (US)

(72) Inventors: Kiarash Alavi, Littleton, CO (US); Ameya Natu, Highlands Ranch, CO (US)

(73) Assignee: Johns Manville, Denver, CO (US)

( * ) Notice: Subject to any disclaimer, the term of this patent is extended or adjusted under 35 U.S.C. 154(b) by 233 days.

(21) Appl. No.: 16/546,448

(22) Filed: Aug. 21, 2019

(65) Prior Publication Data

US 2021/0054171 A1  Feb. 25, 2021

(51) Int. Cl.
| | | |
|---|---|---|
| C08K 5/3445 | (2006.01) | |
| C08L 61/34 | (2006.01) | |
| C08L 61/24 | (2006.01) | |
| C08K 7/14 | (2006.01) | |
| C08G 14/08 | (2006.01) | |
| C08L 61/06 | (2006.01) | |
| C07D 471/08 | (2006.01) | |
| C07D 471/04 | (2006.01) | |

(52) U.S. Cl.
CPC .......... *C08K 5/3445* (2013.01); *C08G 14/08* (2013.01); *C08K 7/14* (2013.01); *C08L 61/06* (2013.01); *C08L 61/24* (2013.01); *C08L 61/34* (2013.01); *C07D 471/04* (2013.01); *C07D 471/08* (2013.01)

(58) Field of Classification Search
CPC ........ C08K 5/3445; C08K 7/14; C08G 14/08; C08G 14/12; C08L 61/24; C08L 61/34; C08L 61/06; C07D 471/04; C07D 471/08; C07D 233/40; C07D 487/04; C07D 487/08
USPC ........................................ 524/106
See application file for complete search history.

(56) References Cited

U.S. PATENT DOCUMENTS

| | | | | |
|---|---|---|---|---|
| 2,764,573 | A | * 9/1956 | Reibnitz | ............ C08G 12/26 |
| | | | | 528/165 |
| 3,663,489 | A | * 5/1972 | Byerley | ............ C08K 5/55 |
| | | | | 521/103 |
| 5,300,562 | A | 4/1994 | Coventry et al. | |
| 5,578,371 | A | 11/1996 | Taylor et al. | |
| 7,323,534 | B2 | * 1/2008 | Arbuckle | ............ C08G 14/08 |
| | | | | 524/541 |
| 7,989,367 | B2 | 8/2011 | Boyer et al. | |
| 2001/0036996 | A1 | 11/2001 | Bristol et al. | |
| 2002/0091185 | A1 | 7/2002 | Taylor et al. | |

(Continued)

*Primary Examiner* — Frances Tischler
(74) *Attorney, Agent, or Firm* — Robert D. Touslee

(57) ABSTRACT

Binder compositions are described that include a phenol, a urea compound, formaldehyde, and at least one cyclic urea-dialdehyde compound. The cyclic urea-dialdehyde compound forms crosslinking bonds between polymers of phenol-urea-formaldehyde when the binder composition is cured. Also described are methods of making fiberglass insulation products using the above-described binder compositions. The methods may include contacting the binder composition with glass fibers and forming an amalgam of the binder composition and the glass fibers. The amalgam may be heated to form mats of the glass fibers and binder. The mats may be processed into the fiberglass insulation products.

20 Claims, 4 Drawing Sheets

(56) References Cited

U.S. PATENT DOCUMENTS

| | | | |
|---|---|---|---|
| 2007/0287018 A1* | 12/2007 | Tutin | D04H 1/64 428/505 |
| 2009/0014034 A1 | 1/2009 | Wang et al. | |
| 2014/0342627 A1 | 11/2014 | Alavi | |

* cited by examiner

UREA-GLYOXAL CROSSLINKING COMPOUNDS FOR PHENOLIC BINDER COMPOSITIONS

BACKGROUND OF THE INVENTION

Fiberglass insulation products contain binders that bind together the individual fibers in order to maintain the products' shape. The binders are rigid, but not so stiff as to resist any bending or compression of the product, particularly when it's being stored and shipped in compacted form to a job site or manufacturing facility. Binders are evaluated on their ability to restore the original shape of the insulation product after an extended period in a compacted form.

Binders made of thermoset polymers are particularly well suited for fiberglass insulation products. They can be made from highly flowable and sprayable aqueous binder compositions that are easy to apply to the fibers, and quickly cured at workable temperatures into rigid thermoset binders that make the insulation product rigid yet compressible. For decades, thermoset binders made of phenol-formaldehyde polymers seemed to provide an ideal choice for their low price, easy application, and good performance in the insulation products. However, phenol-formaldehyde binders suffered from a significant drawback: their tendency to emit free formaldehyde. This presented an acute problem of large formaldehyde emissions in the manufacturing plants where the insulation products were made, and a chronic problem of low-level formaldehyde emissions where the products were installed.

For many types of insulation products, the problem of formaldehyde emissions was solved by switching to binder compositions that didn't include phenol formaldehyde (PF), or related formaldehyde-containing compounds like urea formaldehyde (UF) and phenol-urea-formaldehyde (PUF). These formaldehyde-free binder compositions included acrylic binders, protein-containing binders, and sugar-containing binders. They were acceptable substitutes for phenol formaldehyde binders in several types of fiberglass insulation products, but there was one area where they fell short: insulation products for parts that regularly experienced high temperatures like hot water pipes, internal-combustion engines, and heat-generating appliances like ovens and dishwashers. The new formaldehyde-free binders in contact with these parts often experienced thermal breakdown well before a reasonable end date of the product.

Because phenol-formaldehyde binders can resist thermal breakdown over extended periods, they are still a binder system of choice for parts that regularly experience high temperatures. In order to reduce the formaldehyde emission problem with these binders, various solutions have been tried, including increasing the ratio of phenol relative to formaldehyde (e.g., making novolac PF binders), and adding "formaldehyde scavengers" to the binder compositions. Unfortunately, phenol is much less soluble in water than formaldehyde, so increasing the relative amount of phenol in the binder composition reduces its solubility in water. Alternative organic solvents that more readily dissolve phenol are not commercially practical, or environmentally advisable, in binder compositions for fiberglass insulation products.

Conventional formaldehyde scavengers add cost and reduce binder performance, especially when the scavenger is required to make up a large fraction of the binder composition and serves no other purpose besides formaldehyde scavenging. For example, bisulfite salts are known formaldehyde scavengers, but otherwise contribute little to binder performance as a crosslinking agent or curing catalyst. Binders that are loaded with these salts are also more hydrophilic, which degrades their performance in hot, humid environments.

Additional examples of conventional formaldehyde scavengers include urea, Urea serves a dual function in phenol-formaldehyde binders as both a formaldehyde scavenger and an extender that is incorporated with the phenol and formaldehyde in the cured binder (i.e., PUF binders). However, amount of added urea needs to be precisely matched with the amount of free formaldehyde that's left over from the reaction of phenol and formaldehyde: too little urea results in increased formaldehyde emissions from the cured binder, and too much urea results in excessive ammonia emissions from free urea decomposition. The required matching precision makes urea an unpredictable formaldehyde scavenger, and most phenol-urea-formaldehyde (PUF) binder compositions are supplemented with additional formaldehyde scavengers to insure formaldehyde emission targets are met.

Formaldehyde-substituted ureas and formaldehyde-containing cyclic urea compounds (e.g., triazone) are examples of those additional formaldehyde scavengers. However, scavengers made from formaldehyde substituted ureas and formaldehyde-containing cyclic ureas counterproductively introduce additional formaldehyde to the formaldehyde-containing binder compositions.

Still another approach has been to physically separate the formaldehyde scavenger from the formaldehyde-containing binder composition to prevent it from interfering with the curing and performance of the binder. Examples that use this approach include applying the formaldehyde scavenger to a foil, scrim or facer that gets attached to the binder coated fiberglass. In theory, all the free formaldehyde emitted from the binder gets trapped by the formaldehyde scavenger on the covering sheet before it can escape into the environment. In practice, significant amounts of formaldehyde still escape, especially when the binder compositions are being cured. Thus, there is a need for new approaches to reducing formaldehyde emissions in formaldehyde-containing binder compositions that do not reduce the binder's performance and increase costs. These and other issues are addressed in the present application.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and follows a hyphen to denote one of multiple similar components. When reference is made to a reference numeral without specification to an existing sublabel, it is intended to refer to all such multiple similar components.

BRIEF SUMMARY OF THE INVENTION

Figure 1A:
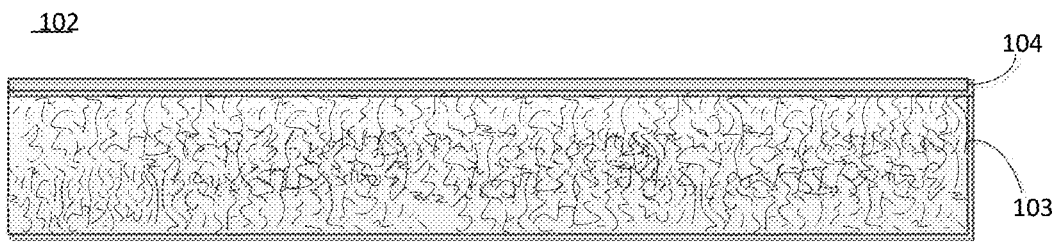
FIGS. 1A-C show simplified illustrations of exemplary composite materials according to selected embodiments.

Formaldehyde-containing binder compositions are described that include one or more cyclic urea-dialdehyde compounds that serve multiple functions in the binder, including formaldehyde scavenger, crosslinker, and polymerization promoter. Because the cyclic urea-dialdehyde compounds do more than just prevent free formaldehyde from escaping the cured binder, they enhance many binder qualities in addition to reducing the binder's formaldehyde emissions. The formaldehyde-containing binder compositions include phenol-formaldehyde (PF), urea-formaldehyde (UF), and phenol-urea-formaldehyde (PUF) compositions that not only cure to binders with significantly reduced formaldehyde emissions, but also have increased tensile strength and lower cure temperatures, among other qualities, than conventional PF binders. The present formaldehyde-containing binders are particularly suited for fiberglass insulation products that insulate parts and structures which are frequently raised to high temperatures (e.g., 30-150° C., 30-100° C.; 30-90° C.; 30-80° C.; 30-70° C.; 30-60° C., etc.).

Exemplary cyclic urea-dialdehyde compounds include both hydroxyl (—OH) groups that react with the phenol-formaldehyde and amido groups that can react with free formaldehyde to form a hydroxymethyl urea group. These reactive groups allow the cyclic urea-dialdehyde compounds to both crosslink with curing PF, UF, or PUF polymer and scavenge free formaldehyde groups. The dual functionality of cyclic urea-dialdehyde compounds as both crosslinking compounds and formaldehyde scavenger provides these compounds with an advantage over single-purpose formaldehyde scavengers that do not enhance the structural characteristics of the binder and fiberglass insulation product.

In addition, the cyclic urea-dialdehyde compounds provide a third function acting as a catalyst that reduces the cure temperature of the PF, UF, and/or PUF binder composition. As shown in the experimental data below, the addition of a cyclic urea-dialdehyde compound to a conventional PF binder composition can lower the cure temperature by as much as 10° C. These lower cure temperatures translate into lower operating temperatures for the curing oven and fast curing times for the binder. Both effects result in higher output and lower operational costs for making fiberglass insulations products with the present binder compositions.

Specific embodiments described in the application include binder compositions that have:
 a phenol;
 a urea compound;
 formaldehyde; and
 at least one cyclic urea-dialdehyde compound.
The cyclic urea-dialdehyde compound forms crosslinking bonds between polymers of phenol-urea-formaldehyde when the binder composition is cured. Because the cyclic urea-dialdehyde compound functions as a formaldehyde scavenger, crosslinker, and catalyst, it is not necessary to add additional compounds to the binder composition that serve these functions. In other words, the binder composition does not have to include an additional formaldehyde scavenger, an additional crosslinking compound, and/or an additional cure catalyst.

Embodiments also include glass fiber insulation products that include glass fibers, and a binder consisting of phenol-urea-formaldehyde polymers crosslinked with at least one cyclic urea-dialdehyde crosslinking compound. As noted above, the cyclic urea-dialdehyde crosslinking compound also functions as a formaldehyde scavenger and catalyst, eliminating the need to include additional compounds with these functions in the binder composition.

Embodiments still further include methods of making fiberglass insulation products with the present binder compositions. The methods include:
 forming an aqueous phenol-formaldehyde mixture;
 adding urea and a cyclic urea-dialdehyde crosslinking compound to the aqueous phenol-formaldehyde mixture to form a phenol-urea-formaldehyde pre-reaction composition;
 adding one or more additional components to the phenol-urea-formaldehyde pre-reaction composition to form a binder composition;
 contacting the binder composition with glass fibers and forming an amalgam of the binder composition and glass fibers;
 heating the amalgam of the binder composition and the glass fibers to form a mat of glass fibers and binder; and
 processing the mat of glass fibers and binder into the fiberglass insulation product.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

DETAILED DESCRIPTION OF THE INVENTION

Additional details are provided about the formaldehyde-containing binder compositions and how they are made, fiberglass-containing products made with the binder compositions, systems for making those fiberglass-containing products, and methods of making those fiberglass-containing products, among other features. As noted above, the formaldehyde-containing binders include one or more a cyclic urea-dialdehyde compounds that can serve multiple functions, including formaldehyde scavenger.

Unless otherwise indicated, the concentrations of the components of the formaldehyde-containing binder compositions are a dry weight percentage that excludes the weight of a binder solvent. In most instances, the present binder compositions are aqueous, and the binder solvent is water. In some exemplary binder compositions, the composition is colorless. The relative concentration of binder solids in the solvent (i.e. total solids) may range from about 5 wt. % to about 75 wt. % based on the total weight of the binder composition. More specific ranges of the total solids include about 5 wt. % to about 50 wt. %; about 10 wt. % to about 70 wt. %; about 10 wt. % to about 40 wt. %; about 30 to about 60 wt. %; about 40 to about 50 wt. %, among other ranges. Specific exemplary total solids concentrations based on the weight of the binder composition include about 10 wt. %, about 15 wt. %, about 20 wt. %, about 25 wt. %, about 30 wt. %, about 35 wt. %, about 40 wt. %, about 45 wt. %, about 50 wt. %, about 55 wt. %; about 60 wt. %; about 65 wt. %; about 70 wt. %; and about 75 wt. %, among other concentrations.

Exemplary Binder Compositions

The formaldehyde-containing binder compositions that have the present cyclic urea-dialdehyde formaldehyde scavengers include phenol-formaldehyde (PF) binder compositions, urea-formaldehyde (UF) binder compositions, and phenol-urea-formaldehyde (PUF) binder compositions, among other formaldehyde-containing binder compositions.

PF binder compositions include resole binder compositions where the amount of formaldehyde (by mole) exceeds the amount of phenol. Phenol-to-formaldehyde mole ratios in these resole binder compositions range from 1:1 to 1:5 (e.g., 1:1.2 to 1:4.5; 1:1.5 to 1:2.5; etc.). The PF binder compositions are aqueous compositions with a total solids concentration of about 30 to 60 wt. % (e.g., 40 to 50 wt. % TS).

The PF resole binders may be made by combining phenol, formaldehyde, and a base that catalyzes the reaction between the phenol and formaldehyde reactants. In one exemplary preparation method, the phenol and formaldehyde are combined as aqueous solutions in a reactor and heated to a temperature of 40-50° C. (e.g., 45° C.) under mechanically agitated (e.g., stirred) conditions. The base catalyst is introduced to the aqueous phenol and formaldehyde mixture over a period of 10-30 minutes. Exemplary base catalysts include alkali metal hydroxides such as sodium hydroxide and potassium hydroxide, alkaline earth metal hydroxides such as magnesium hydroxide and calcium hydroxide, carbonate salts such as sodium carbonate and potassium carbonate, ammonium salts such as ammonium hydroxide, and amines.

The addition of the base catalyst raises the pH of the aqueous phenol and formaldehyde mixture above pH 7 (e.g., pH of 7-10), and can be accompanied by a further increase in reactor temperature (e.g., 70° C.) for 1-2 hours (e.g., 90 minutes). Following this reaction period, the PF reaction mixture may be cooled to room temperature (e.g., 23° C.) and neutralized (e.g., pH 7.2-7.6) by adding an acid (e.g., an inorganic acid such as sulfuric acid). For some applications, the cyclic urea-dialdehyde compound can be added directly to the PF reaction mixture to form the PF binder composition. The cyclic urea-dialdehyde compound can function as a formaldehyde scavenger, crosslinking agent, and cure catalyst that obviates the need to add further compounds with these functions to the binder composition. In these instances, the PF binder composition consists of the pre-cured phenol-formaldehyde compounds, the urea-dialdehyde compound, and any residual materials used in the making of the binder composition (e.g., base catalyst, acidifier, etc.). In additional instances, 1 wt % to 3 wt. % of a latent cure catalyst may be added.

Phenol-urea-formaldehyde (PUF) binders may be made by taking a PF binder composition, either made in situ or purchased commercially, and adding urea. Exemplary preparation methods include adding an aqueous urea solution (or prilled urea) to the PF binder under agitation. The urea may be added in an amount ranging from 15 wt. % to 50 wt. % of the phenol-formaldehyde present in the binder composition. Alternatively, the urea may be added in an amount representing a mole ratio of the urea to free formaldehyde in the PF mixture ranging from 1:1 to 1:1.75.

Ammonia may accompany the addition of urea in the PUF binder compositions. Aqueous ammonia solutions may be added before, during, or after the addition of urea to the PF binder composition. The amount of added ammonia may be measured as a weight percentage of the PF present in the composition (e.g., 1 wt. % to 3 wt. % of the PF amount). The added ammonia alternatively be measured by the change in pH of the PF or PUF binder composition. For example, ammonia and urea may be added to a starting PF composition until its pH increases to around 8.5 (e.g., pH range of 8.2 to 8.6, pH of 8.3, etc.).

In some formulations, the present formaldehyde-containing binder compositions may also include a latent cure catalyst. The cure catalyst is normally added at 0.1% to 5% by dry weight (e.g., 1% to 3% by dry weight) of the binder composition. Exemplary cure catalysts include ammonium and amino salts such as ammonium sulfate, ammonium bisulfate, ammonium phosphate, ammonium sulfamate, ammonium carbonate, ammonium acetate, and ammonium maleate.

The present formaldehyde-containing binder compositions may also include additional polyols. Exemplary polyols include five-carbon and six-carbon sugar alcohols like xylitol, mannitol, and sorbitol. They may be added at levels of about 10 wt. % to 30 wt. % of the total solids in the binder composition. As noted in the experimental results below, the combination of cyclic urea-dialdehydes and sugar alcohols like sorbitol can synergistically increase the scavenging of free formaldehyde and lower the binder cure temperature more than either compound individually.

The present formaldehyde-containing binder compositions may also contain one of more of lubricants (e.g., a mineral oil), thickening and rheology control agents, dyes, and silane coupling agents (e.g., an amino alkyl alkoxysilane such as 3-aminopropyl triethoxysilane). When these processing aids are added to the binder composition, they are typically added in amounts ranging from 1% to 5% by dry weight of the composition.

Exemplary Cyclic Urea-Dialdehyde Compounds

They cyclic urea-dialdehyde compounds in the formaldehyde-containing binder compositions may be formed as a reaction product of (i) a urea compound with (ii) an aldehyde and/or ketone containing compound. The urea compound may be a substituted our unsubstituted urea having the Formula (I):

(I)

where $R_1$, $R_2$, $R_3$, and $R_4$ are independently chosen from a hydrogen moiety (H), an alkyl group, an aromatic group, an alcohol group, an aldehyde group, a ketone group, a carboxylic acid group, and an alkoxy group. Exemplary alkyl groups include straight-chained, branched, or cyclic hydrocarbons of varying size (e.g., $C_1$-$C_{12}$, $C_1$-$C_8$, $C_1$-$C_4$, etc.). Exemplary aromatic (i.e., aryl) groups include substituted or unsubstituted phenyl moieties, among other aromatic constituents. Exemplary alcohol groups include —ROH, where R may be a substituted or unsubstituted, saturated or unsaturated, branched or unbranched, cyclic or acyclic, organic moiety. For example, R may be —$(CH_2)_n$—, where n may be 1 to 12. Exemplary alcohols may also include polyols having two or more hydroxyl groups (—OH) in alcohol group. Exemplary aldehyde groups include —RC(=O)H, where R may be a monovalent functional group (e.g., a single bond), or a substituted or unsubstituted, saturated or unsaturated, branched or unbranched, cyclic or acyclic, organic moiety, such as —$(CH_2)_n$—, where n may be 1 to 12. Exemplary ketone groups may include —RC(=O)R' where R and R' can be variety of carbon containing constituents. Exemplary carboxylic acid groups may include —R—COOH, where R may be a monovalent functional group, such as a single bond, or a variety of carbon-containing constituents. Exemplary alkoxy groups include —$OR_x$, where $R_x$ is an alkyl group.

The aldehyde reactant may include dialdehyde and/or diketone containing compounds may include polyaldehydes (e.g., dialdehydes), polyketones (e.g., diketones), and compounds that have at least two aldehyde groups or at least two ketone groups. Examples include α,β-bicarbonyl compounds where carbonyl carbons are directly bonded as illustrated in the following Formula (II):

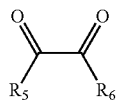
(II)

where $R_5$ and $R_6$ are independently chosen from a hydrogen moiety (H), an alkyl group, or an aromatic group. Exemplary α,β-carbonyl compounds include glyoxal, diacetyl, and benzil (i.e., 1,2-diphenylethane-1,2-dione).

Examples further include α,γ-bicarbonyl compounds where the carbonyl carbons are separated by one carbon atom as illustrated in the following Formula (III):

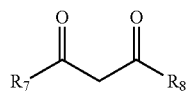
(III)

wherein $R_7$ and $R_8$ are independently chosen from a hydrogen moiety (H), an alkyl group, or an aromatic group. Exemplary α,γ-bicarbonyl compounds include malondialdehyde, and acetylacetone. In some instances, the $R_7$ and $R_8$ groups may independently also include alkoxide groups (—OR) where R represents an alkyl group, and amine groups (—NR'R"), where R' and R" independently represent a hydrogen moiety (H) or an alkyl group. For example, the α,γ-bicarbonyl compounds may include malonic acid esters having Formula (IV):

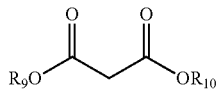
(IV)

where $R_9$ and $R_{10}$ are independently an alkyl group or an aromatic group.

Additional examples of α,γ-bicarbonyl compounds may include those with amide moieties such as those illustrated in Formula (V):

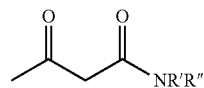
(V)

where R' and R" are independently a hydrogen moiety (H) or an alkyl group.

Additional examples of α,γ-bicarbonyl compounds may further include those with alkoxy moieties such as those illustrated in Formula (VI):

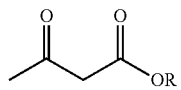
(VI)

where R represents an alkyl group.

Exemplary aldehyde and/or ketone containing compounds may include aldehyde-containing compounds having one or more (e.g., two or more) aldehyde functional groups. Examples of these aldehyde-containing compounds include acetaldehyde, propanaldehyde, butyraldehyde, acrolein, furfural, glyoxal, glutaraldehyde, and polyfurfural among others. Exemplary aldehyde-containing compounds may also include substituted glyoxal compounds having Formula (VII):

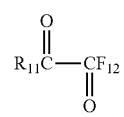
(VII)

where $R_{11}$ and $R_{12}$ may be independently hydrogen (H), an alkyl group, an aromatic group, an alcohol group, an aldehyde group, a ketone group, a carboxylic acid group, and an alkoxy group, among other groups.

The reaction products of the urea compound and the aldehyde and/or ketone containing compound depend on the types of compounds selected, as well as the mole ratio of each compound. For example, when the urea compound is urea and the aldehyde and/or ketone containing compound is glyoxal in a 1:1 mole ratio, the predominant reaction product is 4,5-dihydroxyimidazolidin-2-one (i.e., DHEU) represented by Formula (VIII):

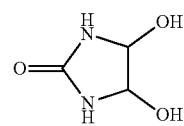
(VIII)

However, when excess urea increases the mole ratio of urea-to-glyoxal to 2:1, the predominant reaction product becomes a glycoluril compound shown in Formula (IX):

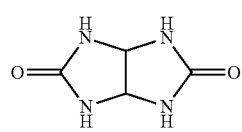
(IX)

Alternatively, when excess glyoxal shifts the mole ratio of urea-to-glyoxal to 1:2, the predominant reaction product becomes a (2R,3S,6R)-2,3,5,6-tetrahydroxy-1,4-diazabicyclo[2.2.1]heptan-7-one compound shown in Formula (X):

(X)

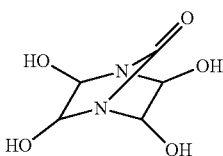

The reaction products of the urea compound and an aldehyde-containing compound having about a 1:1 mole ratio may include imidazolidine compounds of the Formula (XI):

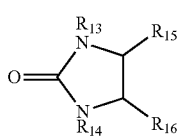

(XI)

where $R_{13}$, $R_{14}$, $R_{15}$, and $R_{16}$ are independently, —H, —OH, —NH$_2$, an alkyl group, an aromatic group, an alcohol group, an aldehyde group, a ketone group, a carboxylic acid group, and an alkoxy group. As noted above, when the reactants are urea and glyoxal, the reaction product may be 4,5-dihydroxyimidazolidin-2-one as shown in Formula (VIII).

Additional examples of reaction products of a urea compound with an aldehyde and/or ketone containing compound may include the reaction products of the above-described α,β-bicarbonyl compounds and α,γ-bicarbonyl compounds as represented by Formulas (XII)-(XVII) below:

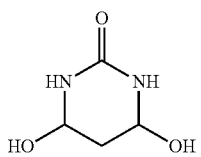

(XII)

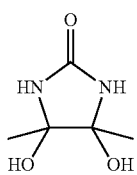

(XIII)

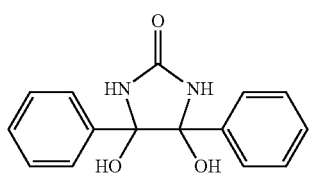

(XIV)

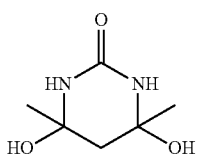

(XV)

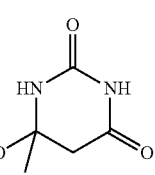

(XVI)

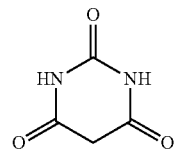

(XVII)

Exemplary Fiberglass-Containing Products

The formaldehyde-containing binder compositions may be used to make fiberglass-containing products that include woven or non-woven glass fibers bound together by a cured matrix of the binder. In some embodiments, they may include one or more additional types of fibers such as carbon fibers, mineral fibers, stone wool fibers, and organic polymer fibers, among other kinds for fibers. The fibers may make up about 50 wt. % to about 99.5 wt. % of the fiberglass-containing products. Additional exemplary fiber weight ranges include about 90 wt. % to about 99 wt. %; and about 75 wt. % to about 95 wt %. At the conclusion of the curing stage, the cured binder may be a water-insoluble, thermoset binder present as a secure coating on the fiber mat at a concentration of approximately 0.5 to 50 percent by weight of the product, for example the cured binder may be present at concentration of approximately 1 to 10 percent by weight of the product. Additional exemplary ranges of the cured binder (as a weight percentage of fiber-containing composite) may include at least about 1 wt. %; at least about 2 wt. %; at least about 3 wt. %; at least about 4 wt. %; at least about 5 wt. %; about 1 wt. % to about 25 wt. %; about 3 wt. % to about 25 wt. %; about 3 wt.T to about 15 wt. %; among other ranges. Specific exemplary amounts of the cured binder as a percentage weight of the fiberglass-containing product may include about 3 wt. %, about 5 wt. %, about 6 wt. %, about 7 wt. %, about 8 wt. %, about 9 wt. %, about 10 wt. %, about 11 wt. %, about 12 wt. %, about 13 wt. %; about 14 wt. %; about 15 wt. %; about 20 wt. %; and about 25 wt. %, among other amounts.

The fiberglass-containing products may take a variety of forms, for example construction materials including piping insulation, duct boards (e.g., air duct boards), and building insulation, reinforcement scrim, and roofing membranes, among other construction materials. Additional examples may include duct liner, duct wrap, flexible duct media, pipe insulation, tank insulation, rigid plenum liner, textile duct liner insulation, equipment liner, oven insulation, elevated temperature board, elevated temperature wrap, elevated temperature panel, insulation batts and rolls, heavy density batt insulation, light density batt insulation, exterior foundation insulation board, and marine hull insulation, among other materials.

The fibers and binder composition, along with the processing conditions, are selected to produce fiber-containing composites with desired physical properties and aging characteristics. For example, when the fiberglass-containing product is a thermal insulation batt, the ordinary (i.e., unweathered) parting strength may be at least about 120 g/g (e.g., at least about 150 g/g). An exemplary range for the ordinary parting strength may be about 120 g/g to about 400 g/g. The weathered parting strength may also be at least about 120 g/g (e.g., at least about 150 g/g), where weathered parting strength is measured after fiberglass-containing product has been subjected to elevated temperature (e.g., about 120° F. or more) and humidity (e.g., about 95% or more relative humidity) for a period of time (e.g. about 7 days, about 14 days, etc.). An exemplary range for the weathered parting strength may be about 120 g/g to about 400 g/g.

Additional physical properties of the fiberglass-containing products may include a density that range of about 5 kg/m$^3$ to about 100 kg/m$^3$. More specific density ranges may include about 5 kg/m$^3$ to about 20 kg/m$^3$; and about 10 kg/m$^3$ to about 80 kg/m$^3$, among other density ranges. Specific exemplary densities of a the fiberglass-containing products may include about 5 kg/m$^3$; about 10 kg/m$^3$; about 15 kg/m$^3$; about 20 kg/m$^3$; about 25 kg/m$^3$; about 30 kg/m$^3$; about 35 kg/m$^3$; about 40 kg/m$^3$; about 45 kg/m$^3$; about 50 kg/m$^3$; about 55 kg/m$^3$; about 60 kg/m$^3$; about 65 kg/m$^3$; about 70 kg/m$^3$; about 75 kg/m$^3$; and about 80 kg/m$^3$, among other densities. Densities for the fiberglass-containing products may vary depending on the type of product made. For example, when the fiberglass-containing product is a thermal insulation batt, a density range of about 4 kg/m$^3$ to about 12 kg/m$^3$ is common, although not the only density range. When the fiberglass-containing product is duct board, a density range of about 30 kg/m$^3$ to about 100 kg/m$^3$ is more typical, although again not the only density range.

The fiberglass-containing products may have a thermal conductivity, A, of less than 0.05 W/mK. An exemplary range of the thermal conductivity for the fiberglass-containing products may include about 0.02 W/mK to about 0.05 W/mK.

Fiberglass-containing products that are thermal insulation batts may have an ordinary (i.e., unweathered) rigidity, as measured by droop level, of about 3 inches or less (e.g., 2.5 inches or less). They may have a weathered droop level of about 5 inches or less (e.g., about 3.5 inches or less). The composites may also have an ordinary recovery level after compression of about 6 inches or more (e.g., 6.5 inches or more). They may have a weathered recovery level of about 5 inches or more (e.g., about 6 inches or more). The droop levels and recovery level ranges may vary depending on the type of fiber-containing composite. For example, a fiberglass-containing product that is duct board may have an ordinary recovery level of about 0.9 inches to about 1.1 inches (although this is not the only range of thickness recovery for duct board).

The fiberglass-containing products may be made to limit the amount of volatile organic compounds (VOCs) emitted from the composites. Exemplary levels of VOC emissions from the fiber-containing composites may be about 1 lb/hour or less (e.g., about 0.8 lb/hour or less).

As noted above, the fibers in the fiberglass-containing products may make up about 50 wt. % to about 99.5 wt. % of the products, with most of the remaining weight being the cured binder. Because the cured binder will burn off the product when it is exposed to intense heat and flame, the loss of weight on ignition of the composite (LOI) may range from about 0.5 wt. % to about 50 wt. %. Additional LOI ranges may be from about 1 wt. % to about 10 wt. %; about 2 wt. % to about 10 wt. %; and about 3 wt. % to about 6 wt. %, among other LOI ranges. LOIs for the fiberglass-containing product may vary depending on the type of product made. For example, when the fiberglass-containing product is a thermal insulation batt, an exemplary LOI range may be about 1 wt. % to about 10 wt. % (although this is not the exclusive range). When the fiberglass-containing product is duct board, a typically LOI range may be about 15 wt. % to about 22 wt. % (although again this is not the exclusive range).

The fiberglass-containing products are water-resistant. Exemplary levels of water absorption in the composites may be about 0.5 wt. % or less, based on the weight of the product. The fiberglass-containing products may also generate reduced levels of particles during transport and installation. For example, when the fiberglass-containing product is thermal insulation batt, it may generate dust levels of about 10 grams to about 50 grams per 10,000 ft$^2$ of the composite. When the fiberglass-containing product is duct board, it may generate dust levels of about 0.03 grams to about 3 grams per pound of the duct board.

Figure 1B:
Figure 1C:
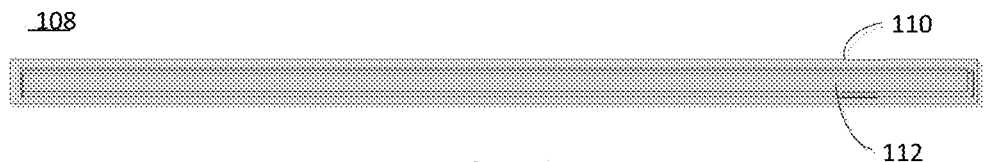

FIG. 1A-C illustrate some of these exemplary fiberglass-containing products. FIG. 1A is a simplified schematic of an exemplary fiberglass-containing batt material 102 that may be used for building, duct, pipe, or part insulation. The material 102 may include a batt 103 of non-woven fibers held together by the binder. The fibers include glass fibers that are used to make the fiberglass insulation (e.g., low-density or high-density fiberglass insulation), or a blend of two or more types of fibers, such as a blend of glass fibers and organic polymer fibers, among other types of fibers. In some examples, a facer 104 may be attached to one or more surfaces of the batt 103. Exemplary thicknesses of the batt 103 may range from about 1 cm to about 40 cm (e.g., about 2 cm to about 30 cm).

FIG. 1B is a simplified schematic of an exemplary fiberglass-containing composite board 106 that may be used as an insulation board, duct board, elevated temperature board, etc. The fibers in board 106 include glass fibers, and may also include one or more types of additional fibers such as organic polymer fibers, carbon fibers, mineral fibers, metal fibers, among other types of fibers, and blends of two or more types of these fibers.

FIG. 1C is a simplified schematic of an exemplary fiberglass-containing flexible insulation material 108 that may be used as a wrap and/or liner for ducts, pipes, tanks, equipment, etc. The fiberglass-containing flexible insulation material 108 may include a facer 110 attached to one or more surfaces of the fiber material 112. Exemplary materials for the facer 110 may include fire-resistant foil-scrim-kraft facing.

Specific examples of fiberglass-containing composites that use the present binder compositions include thermal, thermoset insulation batts, such as low-density fiberglass insulation batt (e.g., less than about 0.5 lbs/ft$^3$) and high-density fiberglass insulation batt. Additional examples include piping insulation, duct boards, duct liner, duct wrap, flexible duct media, pipe insulation, tank insulation, rigid plenum liner, textile duct liner insulation, equipment liner, oven insulation, elevated temperature board, elevated temperature wrap, elevated temperature panel, insulation rolls, exterior foundation insulation board, and marine hull insulation.

Exemplary Systems for Making Fiberglass Products

Figure 2:
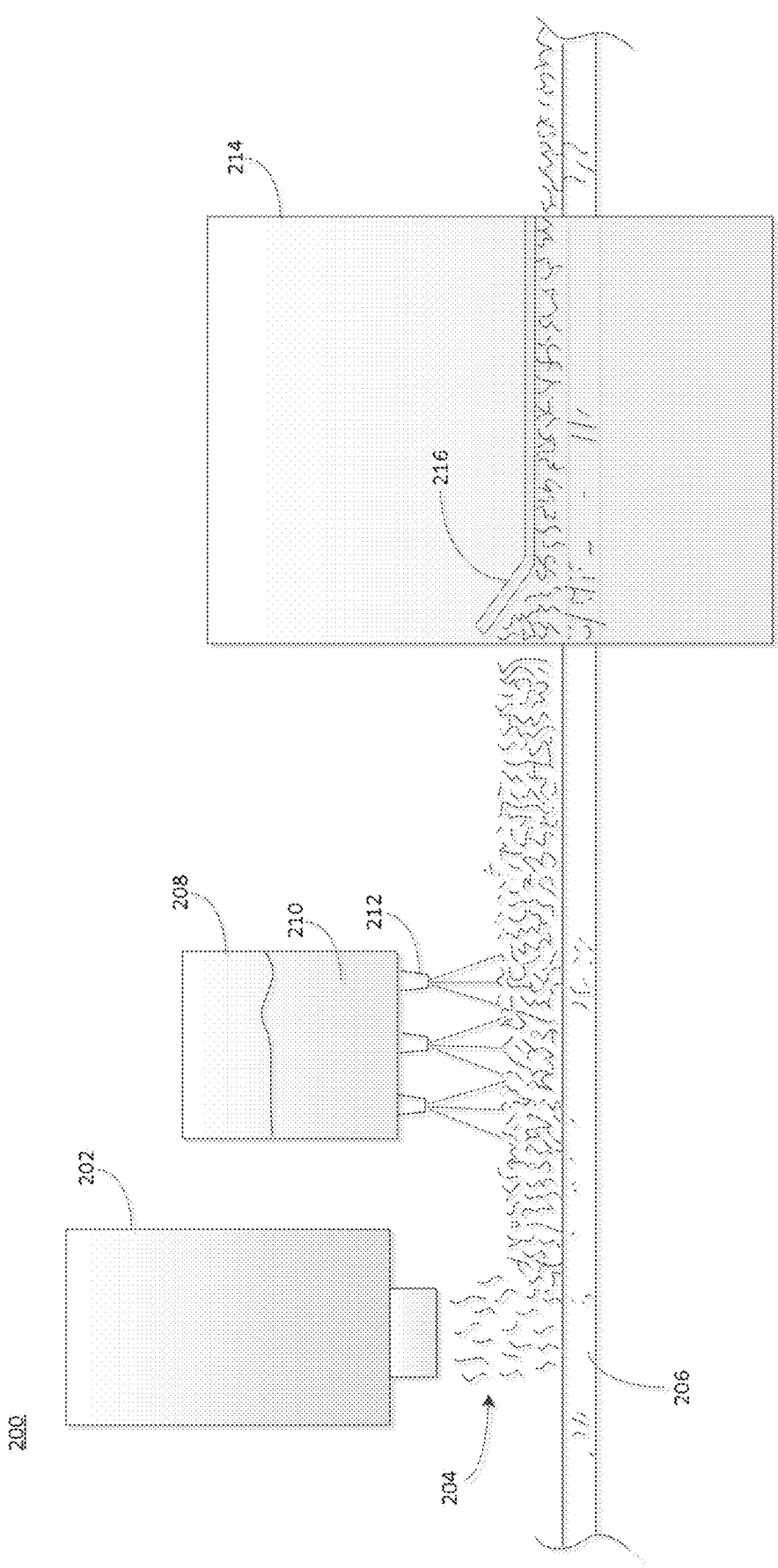
FIG. 2 shows a simplified schematic of an exemplary system for making fiberglass products according to selected embodiments.

FIG. 2 shows a simplified schematic of an exemplary fabrication system 200 for making the fiberglass products described above. The system 200 includes fiber supply unit 202 that supplies the glass fibers for the product. The fiber supply unit 202 may be filled with pre-made glass fibers, or may include equipment for making the glass fibers from starting materials (e.g., molten glass). The fiber supply unit 202 deposits the fibers 204 onto a porous conveyor belt 206 that transports the fibers under the binder supply unit 208.

The binder supply unit 208 contains a liquid uncured binder composition 210, that is deposited onto the fibers 204. In the embodiment shown, the binder composition 210 is spray-coated onto the fibers 204 with spray nozzles 212, however, other application techniques (e.g., curtain coating, dip coating, knife coating, etc.) may be used in addition to (or in lieu of) the spray coating technique illustrated by nozzles 212.

The binder composition 210 applied on fibers 204 forms a fiber and binder amalgam on the top surface of the conveyor belt 206. The belt 206 may be perforated and/or porous to allow excess binder composition 210 to pass through the belt 206 to a collection unit (not shown) below. The collection unit may include filters and circulation pumps to recycle at least a portion of the excess binder back to the binder supply unit 208.

The conveyor belt 206 transports the amalgam to an oven 214 where it is heated to a curing temperature and the binder composition starts to cure. The temperature of the oven 214 and the speed of the conveyor belt 206 can be adjusted to control the curing time and temperature of the amalgam. In some instances, process conditions may set to completely cure the amalgam into the fiberglass composite. In additional instances, process conditions may be set to partially cure the amalgam into a B-staged composite.

The amalgam may also be compressed prior to or during the curing stage. System 200 shows an amalgam being compressed by passing under a plate 216 that tapers downward to decrease the vertical space available to the curing amalgam. The amalgam emerges from under the plate 216 in a compressed state and has less thickness than when it first made contact with the plate. The taper angle formed between the plate 216 and conveyor belt 206 can be adjusted to adjust the level of compression placed on the amalgam. The partially or fully cured product that emerges from under plate 216 can be used for a variety of applications, including construction materials such as pipe, duct, and/or wall insulation, among other applications.

Exemplary Methods of Making Fiberglass Insulation Products

Figure 3:
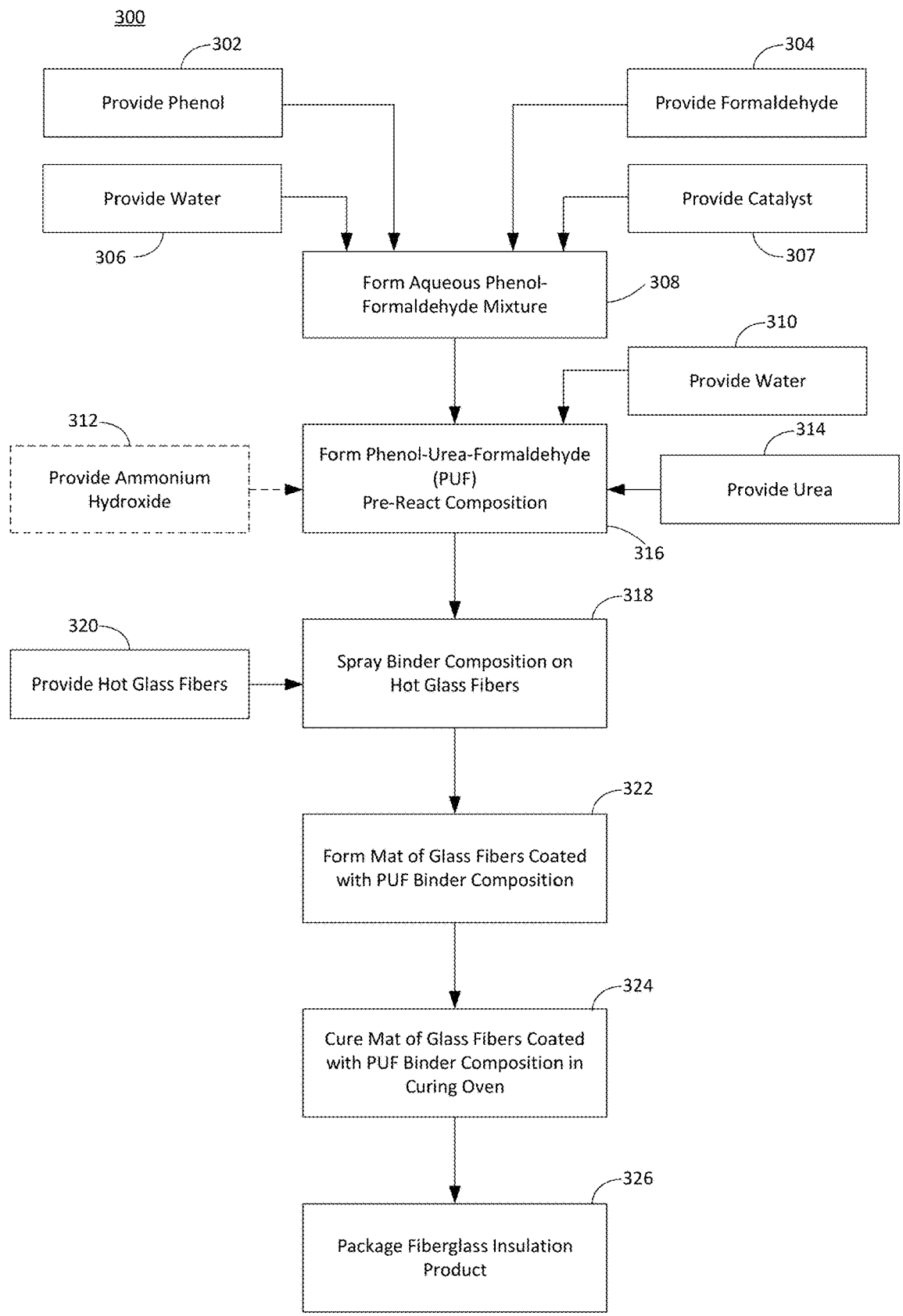
FIG. 3 is a flowchart showing selected components and steps in a method of making a fiberglass insulation product.
Figure 4:
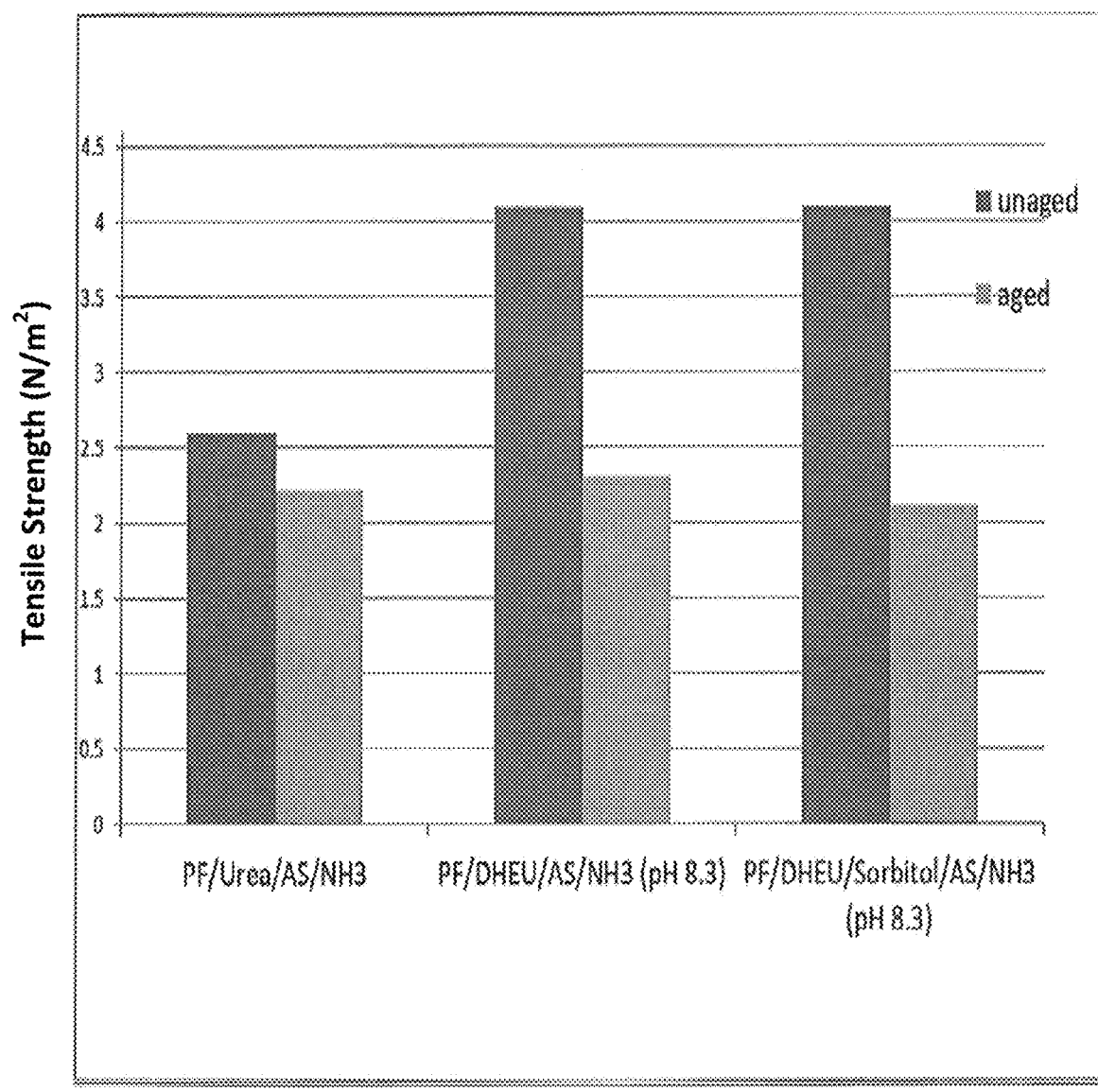
FIG. 4 is a graph of unaged and humid-aged dogbone tensile stress measurement results for selected binders.

FIG. 3 is a flowchart that highlights at least some of the steps in a method 300 of making a fiberglass product with the present binders compositions. The method 300 starts by providing phenol 302, formaldehyde 304, and water 306 to form an aqueous phenol-formaldehyde mixture 308. In some embodiments a cyclic urea-dialdehyde catalyst 307 may also be added as part of the aqueous phenol-formaldehyde mixture. As noted above, the cyclic urea-dialdehyde catalyst 307 also acts as formaldehyde scavenger and crosslinker in the phenol-formaldehyde binder. Exemplary cyclic urea-dialdehyde catalysts 307 include 4,5-dihydroxyimidazoldin-2-one.

The phenol and the formaldehyde may be provided such that they form the phenol-formaldehyde mixture with a formaldehyde-to-phenol molar ratio of about 1.2:1 to about 4.5:1 (e.g., a molar ratio range of 1.5:1 to 2.5:1). The relative quantities of the phenol, formaldehyde, water, and catalyst, may be combined to form the mixture with, for example, a total solids content of about 30 to 60 wt. % of the total weight of the mixture. Another exemplary range is a total solids content of 40 to 50 wt. %.

The phenol-formaldehyde mixture may be formed at an elevated temperature such as 60° C. to 90° C. The pH of the mixture becomes alkaline (e.g., pH ranging from 7 to 9) in those embodiments that include the cyclic urea-dialdehyde catalyst 307 in the aqueous phenol-formaldehyde mixture. For example, when the cyclic urea-dialdehyde catalyst is 4,5-dihydroxyimidazoldin-2-one, the pH of the phenol-formaldehyde mixture normally ranges from 7.5 to 8.5. The cyclic urea-dialdehyde catalyst 307 may be added at 10 wt. % to 50 wt. % of the total solids in the aqueous phenol-formaldehyde mixture. The aqueous mixture may maintain this temperature for 1 minute to 10 hours before more components are added.

Once the mixture has homogenized, urea may be provided to it 310, and optionally ammonium hydroxide may also be provided 312, in addition to more water 314. These additional components transform the original phenol-formaldehyde mixture into a phenol-urea-formaldehyde (PUF) pre-react composition 316. The urea may be added in quantities that bring the weight percentage of the urea relative to the phenol-formaldehyde in the range of 15 wt. % to 50 wt. % (e.g., 20 wt % to 40 wt. %). Additional examples include a so-called "70/30" PUF pre-react composition that has about 70 wt. % phenol-formaldehyde and 30 wt. % urea based on the total weight of the phenol-formaldehyde and urea.

One or more cyclic urea-dialdehyde compounds may be added with or after the urea that forms the PUF pre-react composition. In some embodiments, the cyclic urea-dialdehyde compound is added to a PUF pre-react composition where a cyclic urea-dialdehyde catalyst has not been added. In additional embodiments, the cyclic urea-dialdehyde compound is added to a PUF pre-react composition that already includes a cyclic urea-dialdehyde compound. The cyclic urea-dialdehyde compounds may be added in quantities that make up a significant weight percentage of the PUF pre-react composition on a total solids basis. Exemplary ranges for the amount of the urea-dialdehyde composition on the PUF pre-react composition may include 10 wt. % to 50 wt. % of the total solids in the PUF pre-react composition. Additional exemplary minimum weight percentages of the urea-dialdehyde composition include 15 wt. %, 20 wt. %, 25 wt. %, 30 wt. %, 35 wt. %, 40 wt. %, and 45 wt. %, with the high end of the range at around 50 wt. % based on the total solids in the PUF pre-react composition.

The additional water may be provided to adjust the final concentration of the components of the PUF pre-react composition. Exemplary total solids range for the PUF pre-react composition includes 30 to 60 wt. %, 30 to 50 wt. %, and 40 to 50 wt. % of the total weight of the composition.

The pH of the starting phenol-formaldehyde mixture is maintained or slightly decreases with the addition of the urea and urea-dialdehyde composition to make the PUF pre-react composition. Exemplary pH ranges for the PUF pre-react composition include 7.0 to 9.0 (e.g., 7.5 to 8.5). These initial reactions may also be facilitated by heating the PUF pre-react composition above room temperature. An exemplary temperature range for the PUF pre-react composition includes about 40° C. to about 50° C. The PUF pre-react composition may react at ambient temperature (20-25° C.) or an elevated temperature range (e.g., 40-50° C.) for a period of time ranging from 1 to 12 hours. Additional exemplary time ranges include 2-6 hours, and 8-12 hours, among other ranges.

The PUF pre-react composition may be introduced to a binder table that is also being fed by water and any additional components of the final binder composition. Those additional components may include one or more of a mineral or organic oil to promote dust control of the glass fibers, additional catalysts, additional pH modifiers, coupling agents, such as silane coupling agents, that promote the adhesion of the binder to the glass fibers, thickeners and rheology control agents, coloring agents, and fire retardant agents, among other additional components. The water, PUF pre-react composition, and additional components may be combined under mixing conditions in the binder table to form the binder composition. A total solids concentration of the final binder composition may range from 1 wt. % to 25 wt. % based on the total weight of the binder composition. Additional exemplary ranges include 3 wt. % to 15 wt. %, 10 wt. % to 20 wt. %, and 12 wt. % to 15 wt. %.

The binder composition, which is made at least in part from the PUF pre-react composition, is sprayed on hot glass fibers 318. The hot glass fibers may be provided 320 by a rotating spinner disc that pushes molten glass through rows of tiny orifices in the disc's sidewalls to form the hot glass fibers. A series of nozzles circularly arranged around the hot fibers emerging from the spinner disc spray the binder composition onto the falling glass fibers before they settle on a moving conveyor belt to form a raw mat of fibers coated with the binder composition 322. The volume of binder composition passing through the spray nozzles may be set to produce a target level of binder in the fiberglass product. Exemplary binder levels in the fiberglass product may include 2 wt. % to 25 wt. % (e.g., 2 wt. % to 5 wt. %; 5 wt. % to 10 wt. %; and 15 wt. % to 25 wt. %) as measured by a standard Loss-On-Ignition (LOI) analysis. The heat of the glass fibers evaporates a portion of the water and other volatile compounds from the binder composition, as well as promote the further polymerization of the phenol-formaldehyde-urea compounds as well as crosslinking them with the one or more urea-dialdehyde compounds. In some embodiments, air is blown through the conveyor belt and mat to promote the removal of the water and other volatile compounds from the mat.

The conveyor belt transports the raw mat of fibers and binder composition to a curing oven where the binder composition is more completely cured 324 and additional water and other volatile compounds are removed from the curing fiberglass insulation. The oven temperature may be set to heat the raw mat of fibers and binder composition to a peak curing temperature of about 200° C. (392° F.) to about 260° C. (500° F.). The mat may pass through the curing oven over a period of about 1 minute to 15 minutes. Additional oven curing times may range from about 1.5 minutes to about 2 minutes, and about 5 minutes to 10 minutes.

The cured fiberglass insulation mat emerging from the curing oven may be packaged into a fiberglass insulation product 326. Exemplary products include fiberglass insulation batts, mats, liners, wraps, and boards for a variety of purposes, including building insulation, pipe insulation, appliance insulation, HVAC insulation, and office partitions, among other purposes.

EXPERIMENTAL

A series of modified phenol-formaldehyde binder compositions were made to measure the effects of cyclic urea-dialdehyde compounds on (i) cure temperatures, (ii) formaldehyde emissions, and (iii) tensile strength of the cured binders. The binder compositions were made as follows:

Binder Composition #1—PF+Urea Control

Binder Composition #1 (Control): The binder composition starts by combining a commercially available PF resin (pH of 8.2, 48.5 wt. % total solids, 0.2 wt. % free phenol, 10.8 wt. % free formaldehyde) with urea to make a PF+Urea mixture with an 80/20 molar ratio. The resulting mixture was allowed to react at 25° C. for four hours to form a pre-reacted mixture ("pre-react"). The pre-react was then diluted with water until it became a 30 wt. % aqueous solution. Ammonium hydroxide (28 wt. % solution) was added to the diluted pre-react until the pH climbed to 9.5. The mass ratio of PUF to ammonium hydroxide in the alkaline solution was 100 to 2. An aqueous ammonium sulfate was added to the alkaline solution until the ammonium sulfate was 4 wt. % of the PUF. The addition of ammonium sulfate decreased the pH of the mixture to 8.5. The resulting aqueous mixture was Binder Composition #1, a PF+Urea control binder, that was evaluated for formaldehyde emissions and mechanical performance.

Binder Composition #2—PF+DHEU

Binder Composition #2 started by combining an aqueous solution of the PF+Urea Binder Composition #1 with an aqueous solution of 4,5-dihydroxyl ethylene urea (DHEU). The two aqueous solutions were combined at room temperature (i.e., 23° C.) and stirred for 4 hours to produce Binder Composition #2 having an equal weight of phenol-formaldehyde and DHEU (i.e., a PF:DHEU weight ratio of 50:50).

Binder Composition #3—PF+DHEU+Ammonia

Binder Composition #3 started by mixing an aqueous solution of the PF+Urea Binder Composition #1 with an aqueous solution of 4,5-dihydroxyl ethylene urea (DHEU) to produce a combined solution with a phenol-formaldehyde to DHEU weight ratio of 50:50. The combined solution was diluted to 30 wt. % with the addition of water, and then mixed with a 28 wt. % solution of aqueous ammonia ($NH_4OH$) at room temperature (i.e., 23° C.) and stirred for 4 hours to produce Binder Composition #3 having a PF:DHEU:$NH_3$ weight ratio of 50:50:1. The addition of the ammonia raised the pH of the binder composition to 8.3.

Binder Composition #4—PF+DHEU+AS+Ammonia

Binder Composition #4 started by mixing an aqueous solution of the PF+Urea Binder Composition #1 with an aqueous solution of 4,5-dihydroxyl ethylene urea (DHEU) to produce a combined solution with a phenol-formaldehyde to DHEU weight ratio of 50:50. The combined solution was then diluted to 30 wt. % with the addition of water, and then mixed with a 28 wt. % solution of aqueous ammonia ($NH_4OH$) solution and an ammonium sulfate (AS) solution at room temperature (i.e., 23° C.) and stirred for 4 hours to produce Binder Composition #4 having a PF:DHEU:AS:$NH_3$ weight ratio of 50:50:2:1. The addition of the ammonia and ammonium sulfate raised the pH of the binder composition to 8.3.

Binder Composition #5—PF+DHEU+Sorbitol

Binder Composition #5 started by mixing an aqueous solution of the PF+Urea Binder Composition #1 with an aqueous solution of 4,5-dihydroxyl ethylene urea (DHEU) to produce a combined solution with a phenol-formaldehyde to DHEU weight ratio of 50:50. The combined solution was then mixed with a 70 wt. % sorbitol aqueous solution at room temperature (i.e., 23° C.) and stirred for 4 hours to produce Binder Composition #5 having a PF:DHEU:Sorbitol weight ratio of 35:35:30.

Binder Composition #6—PF+DHEU+Sorbitol+AS

Binder Composition #6 started by mixing an aqueous solution of the PF+Urea Binder Composition #1 with an aqueous solution of 4,5-dihydroxyl ethylene urea (DHEU) to produce a combined solution with a phenol-formaldehyde to DHEU weight ratio of 50:50. The combined solution was then mixed with a 70 wt. % sorbitol aqueous solution and 50 wt. % ammonium sulfate (AS) aqueous solution at room temperature (i.e., 23° C.) and stirred for 4 hours to produce Binder Composition #6 having a PF:DHEU:Sorbitol:AS weight ratio of 40:40:20:2.

Binder Composition #7—PF+DHEU+Sorbitol+AS+Ammonia

Binder Composition #7 started by mixing an aqueous solution of the PF+Urea Binder Composition #1 with an aqueous solution of 4,5-dihydroxyl ethylene urea (DHEU) to produce a combined solution with a phenol-formaldehyde to DHEU weight ratio of 50:50. The combined solution was then mixed with 70 wt. % aqueous solution of sorbitol, 28 wt. % aqueous solution of ammonia, and 50 wt. % aqueous solution of ammonium sulfate (AS) at room temperature (i.e., 23° C.) and stirred for 4 hours to produce Binder Composition #7 having a PF:DHEU:Sorbitol:AS:NH$_3$ weight ratio of 45:45:10:2:1.

Cure Temperature Measurements

Binder Compositions #1-7 were placed in a DMA instrument that increased the temperatures of the binder compositions at a rate of 20° C./minute. The initial curing temperature for each composition was measured and recorded in Table 1 below:

TABLE 1

Cure Temperatures for Binder Compositions #1-7:

| Binder Composition | Binder Components | Weight Ratio | Cure Temperature |
|---|---|---|---|
| 1 | PF:Urea:AS:NH$_3$ | 80:20:4:2 | 169° C. |
| 2 | PF:DHEU | 50:50 | 158° C. |
| 3 | PF:DHEU:NH$_3$ | 50:50:1 | 151° C. |
| 4 | PF:DHEU:AS:NH$_3$ | 50:50:2:1 | 151° C. |
| 5 | PF:DHEU:Sor | 35:35:30 | 171° C. |
| 6 | PF:DHEU:Sor:AS | 40:40:20:2 | 137° C. |
| 7 | PF:DHEU:Sor:AS:NH$_3$ | 45:45:10:2:1 | 164° C. |

Comparing the cure temperatures of Binder Compositions #1 and #4 in Table 1 shows that a PF:DHEU composition can have a cure temperature almost 20° C. lower than a similar PF:Urea composition. Table 1 also shows that additional cure temperature reductions can be achieved for PF:DHEU compositions that use sorbitol and ammonium sulfate.

The significantly reduced cure temperatures for binder compositions that include DHEU demonstrate that these cyclic urea-dialdehyde compounds have catalytic functionality, in addition to their crosslinking and formaldehyde scavenging functionality. Strictly speaking, DHEU and other cyclic urea-dialdehyde compounds cannot be considered pure "catalysts" because they react with and become incorporated into the curing formaldehyde polymers whose polymerization reactions they are catalyzing. Nonetheless, their ability to reduce the activation barrier between other binder reactants and their polymerized products, resulting in a significant lowering of the overall cure temperature, impart what is described here as "catalytic functionality" to these cyclic urea-dialdehyde compounds.

Formaldehyde Emission Measurements

Formaldehyde emission measurements were conducted from solution of Binder Compositions #2 and #5, as well as a control binder composition made from a commercial phenol-formaldehyde binder composition that had no added cyclic urea-dialdehyde compounds like DHEU or added polyols like sorbitol. The measurements were made by monitoring levels of free formaldehyde in the binder solutions using a trapping cartridge/HPLC measurement technique at ambient temperature. A sample of 0.10 g of binder compositions 1-7 was reacted with 2,4-dinotro phenyl hydrazine (DNP) to functionalize free formaldehyde in the binder solutions. The concentration of formaldehyde in each binder solution was evaluated using HPLC. The results are summarized in Table 2:

TABLE 2

Formaldehyde Levels from Select PF Binder Compositions

| Binder Composition | Binder Components | Weight Ratio | Formaldehyde Level (Relative to Control) |
|---|---|---|---|
| 2 | PF:DHEU | 50:50 | 13% |
| 5 | PF:DHEU:Sorbitol | 35:35:30 | 8% |
| Control | PF | 100 | 100% |

The results displayed in Table 2 shows that Binder Composition #2 had an 87% reduction in formaldehyde emissions relative to the PF control binder composition, and Binder Composition #5 had a 92% emissions reduction. These results demonstrate that cyclic urea-dialdehyde compounds like DHEU function as very effective formaldehyde scavengers.

Tensile Strength Measurements

Dogbone tensile strength test measurements were conducted for Binder Compositions #1, #4, and #7 using both unaged and humid-aged conditions. The dogbone samples were made by combining 84 grams of the 30 wt. % solids binder composition in a dogbone mold with 1000 grams of glass beads and curing the sample at 210° C. for 10 minutes. The test results are summarized in the graph of FIG. 2 and Table 3 below:

TABLE 3

Tensile Strength Test Results

| Binder Composition | Binder Components | Weight Ratio | Tensile Strength (N/m$^2$) | |
|---|---|---|---|---|
| | | | Unaged | Aged |
| 1 | PF:Urea:AS:NH$_3$ | 80:20:4:2 | 2.6 | 2.2 |
| 4 | PF:DHEU:AS:NH$_3$ | 50:50:2:1 | 4.1 | 2.3 |
| 7 | PF:DHEU:Sor:AS:NH$_3$ | 45:45:10:2:1 | 4.1 | 2.1 |

The dogbone test results show that the presence of a cyclic urea-dialdehyde compound like DHEU can increase unaged tensile strength of the cured binder by as much as 60% compared to a cured PUF binder lacking the compound. These test results demonstrate that cyclic urea-dialdehyde compounds like DHEU function as very effective crosslinking agents that improve the tensile strength of the cured binders.

Binder Composition #8: PUF+20% DHEU

A PUF binder solution was made with dissolving 30 g urea in 144.33 g of a 48.3% solution of commercial PF (used in Binder Composition #1) such that the molar ratios of PF/urea were 70/30. The binder composition was allowed to pre-react at 25 C for two hours to generate PUF. To this PUF enough DHEU was added such that the mass ratios of PUF/DHEU were 80/20. Hand sheets and dog bones were made immediately after the PUF/DHEU were mixed to minimize exposure of PUF to DHEU mimicking a potential 2-component system made from PUF and DHEU.

Binder Composition #9: PUF+30% DHEU

The experiment above with Binder Composition #8 was repeated but the mass ratios of PUF/DHEU was changed to 70/30. Hand sheets and dog bones were made immediately after the PUF/DHEU were mixed to minimize exposure of PUF to DHEU mimicking a potential 2-component system made from PUF and DHEU.

Binder Composition #10: PUF+Ammonium Hydroxide+ 20% DHEU

A PUF-ammonia binder solution was made with dissolving 30 g urea in 144.33 g of a 48.3% solution of commercial PF (used in Binder Composition #1) such that the molar ratios of PF/urea were 70/30. To this pre-react added enough ammonium hydroxide to increase the pH to 8.5. The binder composition was allowed to pre-react at 25 C for two hours to generate PUF. To this PUF enough DHEU was added such that the mass ratios of PUF/DHUE were 80/20. Hand sheets and dog bones were made immediately after the PUF/DHEU were mixed to minimize exposure of PUF to DHEU mimicking a potential 2-component system made from PUF and DHEU.

Binder Composition #11: PUF+Ammonium Hydroxide+ 30% DHEU

A PUF-ammonia binder solution was made with dissolving 30 g urea in 144.33 g of a 48.3% solution of commercial PF (used in Binder Composition #1) such that the molar ratios of PF/urea were 70/30. To this pre-react added enough ammonium hydroxide to increase the pH to 8.5. The binder composition was allowed to pre-react at 25 C for two hours to generate PUF. To this PUF enough DHEU was added such that the mass ratios of PUF/DHUE were 70/30. Hand sheets and dog bones were made immediately after the PUF/DHEU were mixed to minimize exposure of PUF to DHEU mimicking a potential 2-component system made from PUF and DHEU.

Formaldehyde emission measurements were conducted during the curing of Binder Compositions #8—#11, as well as a control binder composition (#1) made from a commercial phenol-formaldehyde binder composition that had no added cyclic urea-dialdehyde compounds like DHEU or added polyols like sorbitol. The measurements were made by monitoring gaseous formaldehyde emissions using a trapping cartridge/HPLC measurement technique as the binder compositions were cured at 232° C. for 10 minutes. The experiments were carried as follows: A 10 g solution containing 30% binder solids (PUF, PUF/DHEU or PUF/Ammonia/DHEU) was transferred to a crucible containing 20 g unbonded fiber glass. The crucible was placed in a tube furnace at 232 C for 10 minutes while being purged with air. The evolved gasses were passed through a heated stainless steel tube heated to 150 C to a trapping cartridge where formaldehyde functionalized with dinitro phenyl hydrazine (DNP) and injected into a HPLC which determined the level of formaldehyde emission. The results are summarized below in Table 4.

TABLE 4

Formaldehyde Levels from Select PF Binder Compositions

| Binder Composition | Binder Components | Weight Ratio | Emission Level (Relative to Control) |
|---|---|---|---|
| 8 | PUF:DHEU | 80/20 | 78% |
| 9 | PUF:NH3/DHEU | 80/3/20 | 74% |
| 10 | PUF:DHEU | 70/30 | 23% |
| 11 | PUF:NH3/DHEU | 70/3/30 | 35% |
| Control | PUF | 100 | 100% |

Table 4 shows that addition of ammonium hydroxide to the DHEU systems has minimum effect on the formaldehyde emission during cure of the PUF resin.

Formaldehyde emissions from product were evaluated according to "Standard Method for the Testing and Evaluation of Volatile Organic Emissions from Indoor Sources Environmental Chambers", CDPH/EHLB/Standard Method V1.1. (February 2010), California Specification 01350). Duct Liner (1" thickness) was manufactured with resin content of 16%. Control was standard PUF at PF/urea pre-react ratios of 70/30. Formaldehyde emissions are presented in Table 5.

TABLE 5

Formaldehyde Emissions from Duct Liner

| Binder Components | Weight Ratio | Emission Level (Relative to Control) |
|---|---|---|
| PUF | 100 | 100% |
| PUF:DHEU | 70/30 | 53% |
| PUF/DHEU | 80/20 | 64% |

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the compound" includes reference to one or more compounds and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A fiberglass insulation product comprising:
   glass fibers formed into a fiberglass mat or batt; and
   an aqueous binder comprising phenol-urea-formaldehyde polymers crosslinked with a reaction product of urea and glyoxal, and a polyol comprising a five-carbon or six-carbon sugar alcohol;
   wherein the binder is formed from a binder composition that includes a base catalyst and a latent cure catalyst; and
   wherein the glass fibers are 50 wt. % to 99.5 wt. % of the fiberglass insulation product.

2. The fiberglass insulation product of claim 1, wherein the base catalyst is selected from the group consisting of sodium hydroxide, potassium hydroxide, magnesium hydroxide, calcium hydroxide, sodium carbonate, potassium carbonate, and ammonium hydroxide.

3. The fiberglass insulation product of claim 1, wherein the binder is formed from a binder composition characterized by a mole ratio of urea to free formaldehyde ranging from 1:1 to 1:1.75.

4. The fiberglass insulation product of claim 1, wherein the binder is formed from a binder composition that includes ammonia.

5. The fiberglass insulation product of claim 4, wherein the binder is formed from a binder composition characterized by a pH ranging from 8.2 to 8.6.

6. The fiberglass insulation product of claim 1, wherein the latent cure catalyst is selected from the group consisting of ammonium sulfate, ammonium bisulfate, ammonium phosphate, ammonium sulfamate, ammonium carbonate, ammonium acetate, and ammonium maleate.

7. The fiberglass insulation product of claim 1, wherein the fiberglass insulation product further comprises additional fibers selected from the group consisting of carbon fibers, mineral fibers, stone wool fibers, and organic polymer fibers.

8. The fiberglass insulation product of claim 1, wherein the fiberglass insulation product is characterized by an ordinary parting strength of at least 120 g/g.

9. The fiberglass insulation product of claim 1, wherein the fiberglass insulation product is characterized by a density of about 5 kg/m³ to about 100 kg/m³.

10. The fiberglass insulation product of claim 1, wherein the fiberglass insulation product is characterized by an ordinary recovery level after compression of greater than or about 6 inches.

11. The fiberglass insulation product of claim 1, wherein the fiberglass insulation product is characterized by an amount of volatile organic compound emissions that is less than or about 1 lb/hour.

12. The fiberglass insulation product of claim 1, wherein the fiberglass insulation product is characterized by a water absorption level that is less than or about 0.5 wt. % based on a weight of the fiberglass insulation product.

13. The fiberglass insulation product of claim 1, wherein the fiberglass insulation product is a construction material.

14. The fiberglass insulation product of claim 13, wherein the construction material is selected from the group consisting of piping insulation, duct board, building insulation, reinforcement scrim, and roofing membranes.

15. A fiberglass insulation product comprising:
   glass fibers formed into a fiberglass mat or batt; and
   an aqueous binder comprising phenol-urea-formaldehyde polymers crosslinked with a reaction product of urea and glyoxal, and a polyol,
   wherein the binder is formed from a binder composition that includes a base catalyst and a latent cure catalyst; and
   wherein the glass fibers are 50 wt. % to 99.5 wt. % of the fiberglass insulation product, and
   wherein the polyol is present at from 10 wt. % to 30 wt. % of the total solids in the binder composition.

16. The fiberglass insulation product of claim 15, wherein the base catalyst is selected from the group consisting of sodium hydroxide, potassium hydroxide, magnesium hydroxide, calcium hydroxide, sodium carbonate, potassium carbonate, and ammonium hydroxide.

17. The fiberglass insulation product of claim 15, wherein the binder is formed from a binder composition characterized by a mole ratio of urea to free formaldehyde ranging from 1:1 to 1:1.75.

18. The fiberglass insulation product of claim 15, wherein the binder is formed from a binder composition characterized by a pH ranging from 8.2 to 8.6.

19. The fiberglass insulation product of claim 15, wherein the latent cure catalyst is selected from the group consisting of ammonium sulfate, ammonium bisulfate, ammonium phosphate, ammonium sulfamate, ammonium carbonate, ammonium acetate, and ammonium maleate.

20. The fiberglass insulation product of claim 15, wherein the fiberglass insulation product is a construction material.

* * * * *